United States Patent

Fitch et al.

[11] Patent Number: 5,708,198
[45] Date of Patent: Jan. 13, 1998

[54] FERROUS PARTICLE COUNTER

[75] Inventors: James C. Fitch; Stuart D. Bents, both of Tulsa, Okla.

[73] Assignee: Diagnetics, Inc., Tulsa, Okla.

[21] Appl. No.: 647,335

[22] Filed: May 9, 1996

Related U.S. Application Data

[63] Continuation-in-part of Ser. No. 467,851, Jun. 6, 1995, abandoned, which is a continuation of Ser. No. 210,871, Mar. 17, 1994, abandoned.

[51] Int. Cl.$^6$ ............................................. G01N 33/30
[52] U.S. Cl. ............................................. 73/61.42
[58] Field of Search ........................ 73/61.41, 61.42, 73/61.71, 61.72, 61.73, 865.5, 53.07; 210/222, 223; 324/204; 340/631

[56] References Cited

U.S. PATENT DOCUMENTS

| | | | |
|---|---|---|---|
| 2,105,851 | 1/1938 | Vobach et al. | 73/51 |
| 2,452,220 | 10/1948 | Bower | 210/1.5 |
| 2,464,628 | 3/1949 | Willard | 209/232 |
| 3,093,998 | 6/1963 | Albertson et al. | 73/61 |
| 3,627,678 | 12/1971 | Marston et al. | 210/222 |
| 3,873,448 | 3/1975 | Isberg et al. | 210/222 |
| 3,887,457 | 6/1975 | Marston et al. | 210/222 |
| 4,047,814 | 9/1977 | Westcott | 356/38 |
| 4,298,478 | 11/1981 | Watson et al. | 210/695 |
| 4,375,407 | 3/1983 | Kronick | 209/8 |
| 4,492,921 | 1/1985 | Sandulyak et al. | 324/204 |
| 4,500,839 | 2/1985 | Jones et al. | 324/204 |
| 4,841,244 | 6/1989 | Chambers | 324/204 |
| 5,053,344 | 10/1991 | Zborowski et al. | 436/177 |
| 5,095,740 | 3/1992 | Hodgson et al. | 73/61 |
| 5,122,269 | 6/1992 | De Reuver | 210/222 |
| 5,380,091 | 1/1995 | Buchanan | 374/16 |

FOREIGN PATENT DOCUMENTS

| | | |
|---|---|---|
| 987-471-A | 4/1981 | U.S.S.R. |
| 1659-784-A | 10/1988 | U.S.S.R. |
| WO 87/03368 | 6/1987 | WIPO |

*Primary Examiner*—Michael Brock
*Attorney, Agent, or Firm*—Head, Johnson & Kachigian

[57] ABSTRACT

A method of and apparatus for determining ferrous particle counts in a fluid within a machine fluid system. In a sequential process, a solid particle count in a fluid above at least one given particle size is determined to determine particle size distribution. Ferrous particles are separated from the fluid and a solid particle count in the fluid above at least one given particle size is again measured to determine the solid contamination level of non-ferrous particles only. The solid particle count is compared with the non-ferrous particle count to determine the ferrous particle count above at least one given particle size to determine particle size distribution in said machine fluid system caused by wear.

13 Claims, 4 Drawing Sheets

FERROUS PARTICLE COUNTER

CROSS-REFERENCE OF APPLICATION

This is a continuation-in-part application of Ser. No. 467,851, filed Jun. 06, 1995, now abandoned, entitled "Ferrous Particle Counter" which is incorporated herein by reference which is a file wrapper continuing patent application of U.S. patent application Ser. No. 08/210,871 filed on Mar. 17, 1994. now abandoned

BACKGROUND OF THE INVENTION

1. Field of the Invention

The present invention relates to a method and apparatus to determine ferrous particle counts in a fluid. In particular, the present invention relates to a method and apparatus for real time fluid sampling to quantitatively determine ferrous particle counts and particle size distribution.

2. Prior Art.

Analysis of the fluid in a fluid system is important in recognizing the symptoms of impending machine failure.

The presence of excessive amounts of wear and cavitation debris in a fluid system are tell-tale signs of an impending component failure. Maintenance should ideally be scheduled before harm to other components and catastrophic failure results. Predictive maintenance or condition monitoring is, then, a way to achieve cost savings on equipment and labor expenses.

There are numerous ways to determine solid particle contamination in a fluid system although many of these determine total solid contamination which includes dirt, dust and other debris. It is often desirable to determine the size and number of ferrous particles above one or more sizes in the fluid system.

The traditional ways to evaluate the presence of wear metal are by spectrographic elemental analysis, ferrographic analysis, and various magnetic concentration detectors. None of these techniques provide any automatic determination of wear particles above one or more sizes.

In ferrography, ferrous particles are magnetically deposited on a laboratory slide and viewed under a microscope. Its use is generally limited to laboratory analysis from sample bottles. Analytical ferrography is not a quantitative technique.

Spectrographic analysis can be used to establish and quantify the presence of wear metals and additives in fluids. This may be accomplished through atomic emission, atomic absorption, or inductive coupled plasma spectrometry. The technique is limited in its ability to count and size particles and is unable to access elements from particles larger than 8 microns.

Magnetic concentration detectors use a magnetic technique to estimate ferrous levels as a density (for example, ppm, or umg/ml) but are unable to count and size ferrous particles.

These existing methods of analysis are typically relegated to laboratory analysis.

There remains a need to provide a device and a method for determining the ferrous particle contamination in the field and laboratory specifically as a measure of count and size.

It is additionally advantageous to provide a method and apparatus to determine ferrous particle contamination in a fluid by probing on to a fluid system.

It is additionally advantageous to provide a method and apparatus to determine ferrous particle contamination that will operate in conjunction with various solid contamination measurement devices and particle counters.

It is also advantageous to provide a method and an apparatus to determine ferrous particle contamination in-line in a fluid system.

It is, therefore, a principal object and purpose of the present invention to determine ferrous particle sizes and counts in a fluid.

It is an additional object and purpose of the present invention to dynamically determine ferrous particle sizes and counts in a fluid in the field.

It is a further object and purpose of the present invention to determine ferrous particle sizes and counts in-line in a fluid system.

SUMMARY OF THE INVENTION

The present invention provides an apparatus and method to determine ferrous particle contamination in a fluid within a machine fluid system and is used along with a solid particle counter apparatus.

A sampling probe on the device connects to the fluid system. The sampling probe is, in turn, connected to an adapter. The sampling probe and adapter each have axial openings which together form a passageway from the fluid system into a separator chamber. The separator chamber is filled with a ferrous mesh media. The separator chamber is, in turn, in fluid communication with an adapter having an axial passage. Finally, the axial passage is in fluid connection with a test port.

A magnet induces a magnetic field which passes through the separator chamber. The ferrous mesh media, thus, becomes magnetized. As fluid passes through the chamber, ferrous particles are drawn toward and suspended by the media.

In order to determine the ferrous particle contamination in the fluid, two measurement readings are taken.

A solid contamination level is determined by measuring the solid particulate contamination in the fluid. The test port of the apparatus is connected with a particle counting apparatus which includes a test screen to provide mechanical filtration of particulate matter.

During a measurement test, fluid will pass through the screen leaving particles on the screen surface. The particles gradually close off available pores and flow through the screen is thereby reduced. The speed or velocity of a test piston is sensed or picked up by a linear gauge and relayed to a data acquisition unit. The test piston will slow down as the particulate matter accumulates on the screen. The information on the change in speed on the test piston as the fluid moves is used to determine and calculate the particulate count of contamination in the fluid.

Another measurement is taken with the ferrous particle contamination device inserted between the contamination measurement apparatus and the fluid system. As fluid passes through the separator chamber, any ferrous particles will be drawn to and captured by the wire mesh media which has been induced with a magnetic field.

Accordingly, only non-ferrous particles will pass into the particle counting apparatus.

Finally, the total solid particulate counts is measured against the non-ferrous solid particulate counts. The difference between the two measurements results in the ferrous particulate counts level in the fluid.

DETAILED DESCRIPTION OF THE PREFERRED EMBODIMENTS

Figure 1:
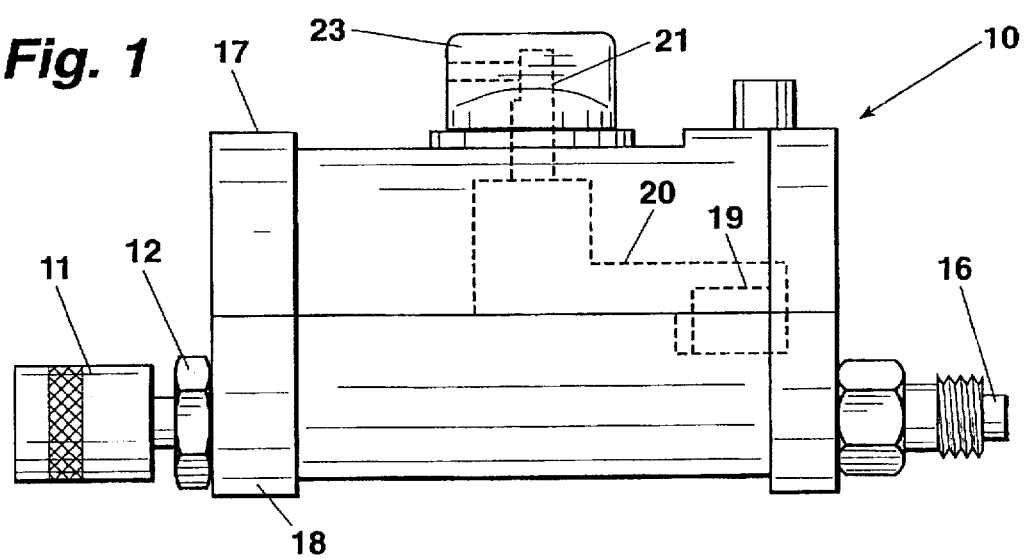
FIG. 1 is an elevation view of an apparatus for determining ferrous particle contamination in a fluid constructed in accordance with the present invention.
Figure 2:
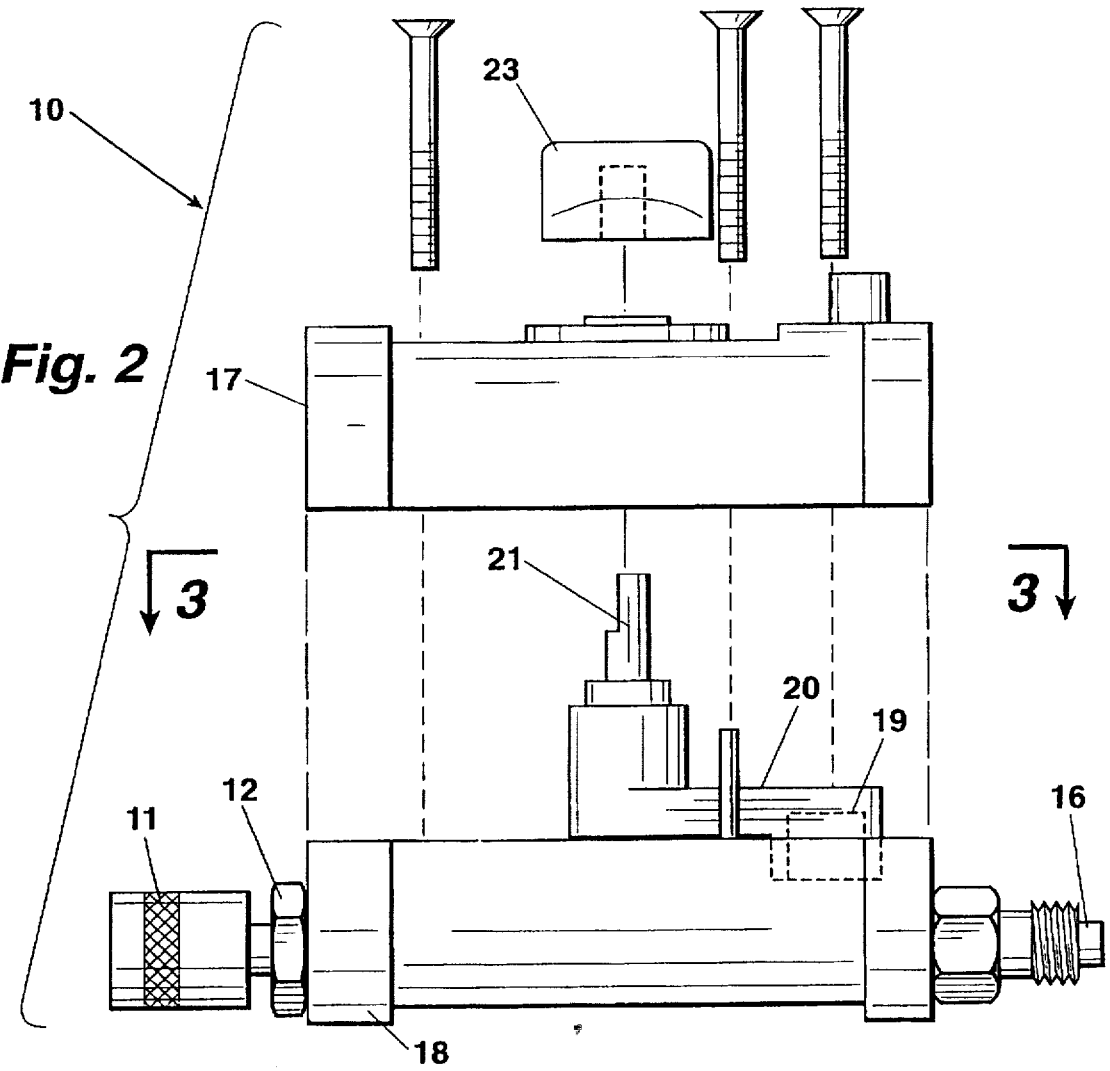
FIG. 2 is an exploded view of the ferrous particle contamination apparatus as shown in FIG. 1.

Referring to the drawings in detail, FIG. 1 is an elevation view of a device 10 used in determining ferrous particle counts in a fluid within a machine fluid system caused by wear. FIG. 2 is an exploded view of the device 10 shown in FIG. 1. The device is used with a solid particle count measurement apparatus to be described herein.

The invention includes a sampling probe 11 having internal threads which will connect to a port (not shown in FIG. 1-4) on a fluid system, such as a hydraulic system. The present invention has numerous applications in various fluid systems. In this way, the device 10 may be used in-line with a fluid system.

The sampling probe 11, is, in turn, connected to an adapter 12. The sampling probe 11 terminates in an end having external threads which mate with internal threads in adapter 12.

Figure 3:
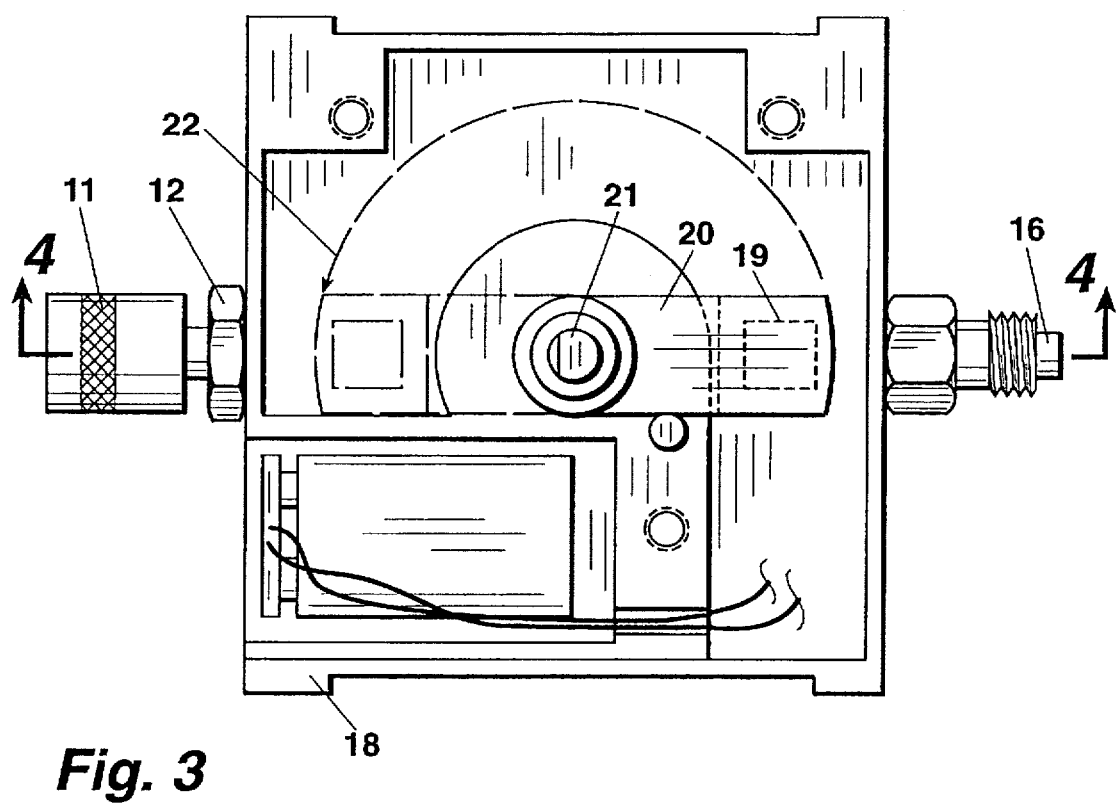
FIG. 3 is a sectional view of the ferrous particulate contamination apparatus taken along section line 3—3 of FIG. 2.
Figure 4:
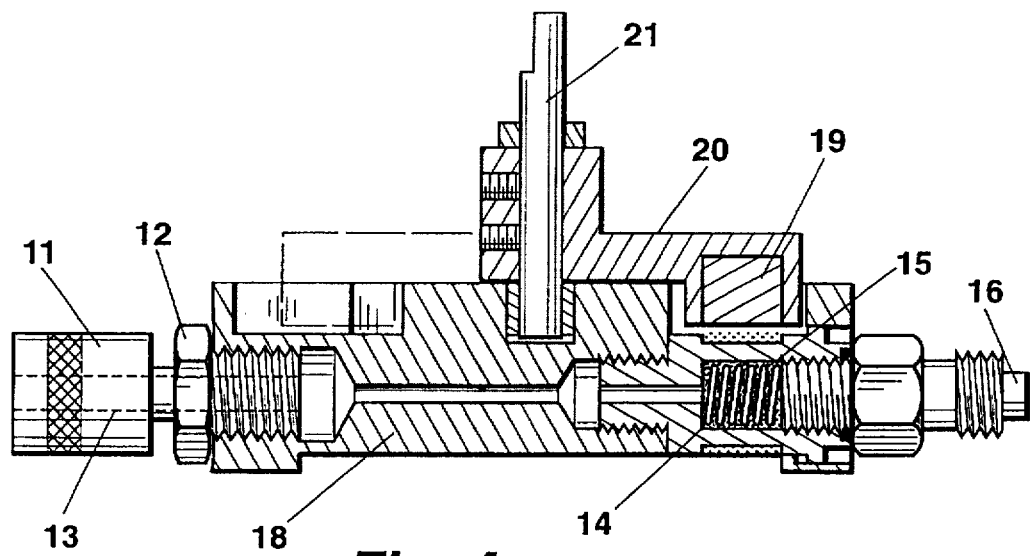
FIG. 4 is a sectional view of the ferrous particle contamination apparatus taken along section line 4—4 of FIG. 3.

FIG. 3 is a sectional view taken along section line 3—3 of FIG. 2 while FIG. 4 is a sectional view taken along section line 4—4 of FIG. 3.

As best seen in FIG. 4, the sampling probe 11 and adapter 12 each having axial openings which together form a passageway 13 from the fluid system into a separator chamber 14. A source of fluid from the fluid system to be monitored is, thus, supplied.

The separator chamber 14 is filled with a ferrous mesh media 15. While a mesh media is employed, it will be understood that other ferrous media, such as single screens or wafers might be used. The separator chamber 14 is, in turn, in fluid connection with a test port 16. When a contamination measurement is not being taken, the test port 16 may be closed off by a threaded end (not shown).

Fluid entering the sampling probe 11 from the fluid system is under pressure. It will, thus, be seen that fluid entering the sampling probe 11 will be allowed to pass into and through the device 10.

A housing formed of two halves 17 and 18 surrounds the separator chamber and passage.

A magnet 19, external to the separator chamber, is held by at the end of a radial rotor arm 20. The rotor will rotate about shaft 21 which acts as its axis. The magnet 19 is thus allowed to travel in a radial path shown by arrow 22. The magnet 19 is secured by retained compound and a set screw.

The shaft 21 passes through an opening in the body half 17 and terminates in a knob 23. Rotation of the knob will move the rotor arm and the magnet 19.

The magnet 19 induces a magnetic field which passes through the separator chamber 14 wherein the position in FIGS. 1-4. The ferrous mesh media 15, thus, becomes magnetized. As fluid passes through the separator chamber, ferrous particles are drawn toward and suspended by the media.

Rotating the rotor arm 20 one hundred and eighty degrees (180°) moves the magnetic field from the separator chamber.

While a ½ cube magnet is shown in the embodiment in FIGS. 1-3, other types of permanent magnets may also be employed. It will also be recognized that an electromagnet, that would be activated as desired, could also be used.

The separator chamber 14 is constructed of aluminum or other non-ferrous material so that it will not become magnetized itself. The diameter of the chamber is significantly larger than any of the passages through the device 10. This causes the velocity of fluid in the separator chamber 14 to be reduced from that in the passages. It will, thus, require less magnetic force to pull out and retain ferrous particles from the fluid.

Figure 6:
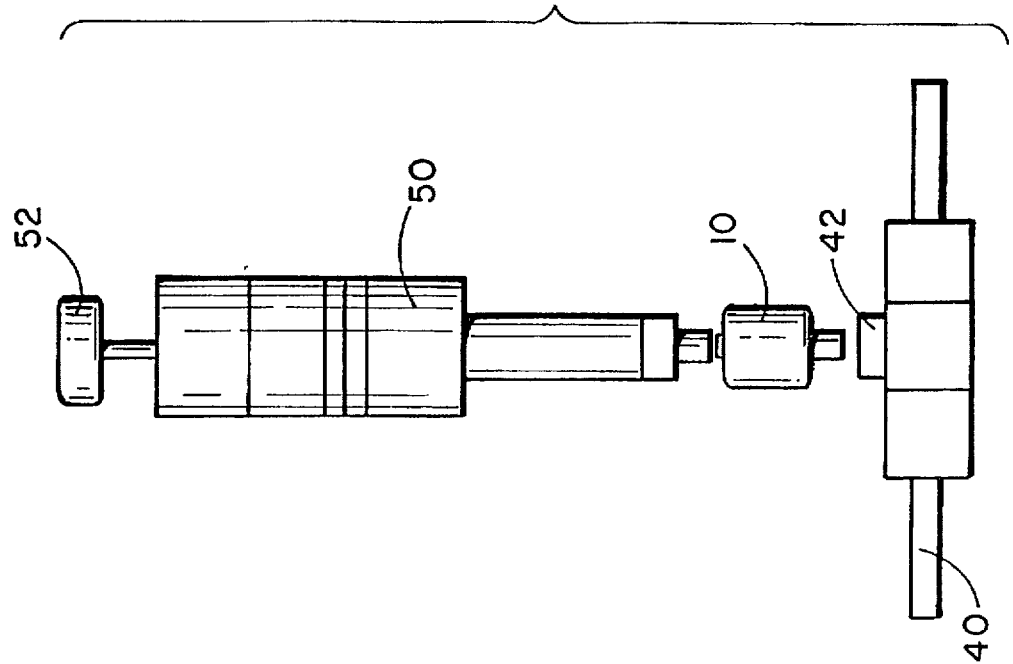
FIGS. 5 and 6 diagrammatically illustrate the process used to determine ferrous particle contamination in a fluid as taught by the present invention.
Figure 5:
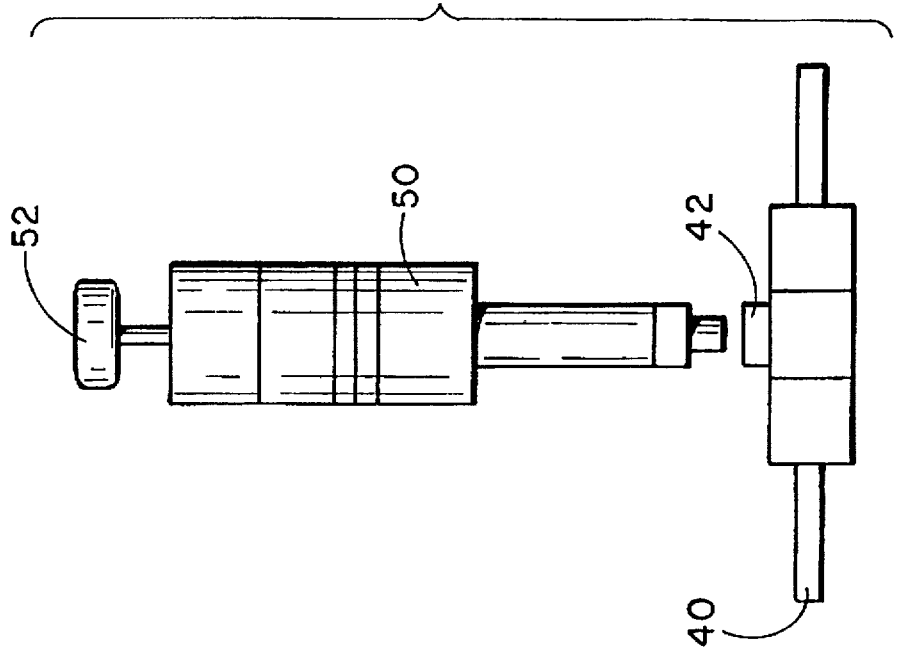

FIGS. 5 and 6 diagrammatically illustrate one process used to determine the ferrous particle contamination level in the fluid. A first measurement reading is taken as illustrated in FIG. 5, followed by a second measurement reading as illustrated in FIG. 6. It will be appreciated that the measurement readings may be taken in reverse order and a comparison made.

Fluid from the system would be directed into and through an inlet line 40 to an inlet port 42 having a threaded connection. A first solid contamination level is determined by measuring the solid particulate contamination in the fluid.

Particle size distribution of particulate matter in a fluid is today the most acceptable way of expressing the level of contamination. There are various known ways of determining solid particle size distribution in the fluid using particle counting devices, such as light blockage, light scattering, and pressure rise/pore blockage.

The contamination measurement apparatus 50 of the present invention includes a test screen to provide mechanical filtration of particulate matter in order to determine solid contamination levels in the fluid. One such measurement apparatus is illustrated in Hodgson et al, U.S. Pat. No. 5,095,740 although many other types of solid contamination measurement devices may be used.

During a measurement test, fluid will pass through the screen leaving particles on the screen's surface. The particles gradually close off available pores and flow through the screen is thereby reduced. On the opposite side of the test screen is a passageway leading to a cylindrical test chamber. A test piston is allowed to move within the test chamber. The test piston is linked to a linear gauge which moves in response to the piston rod. Linear movement of the test piston will, thus, move the linear gauge linearly. Other analytical gauges could be used to track the position of the test rod.

In the measurement stroke, pressurized fluid in the system will be allowed to pass through the test screen and cause the test piston to move. The speed or velocity of the moving test piston is sensed or picked up by the linear gauge and relayed to a data acquisition unit. The test piston rod will slow down as the particulate matter accumulates on the screen. The information on the change in speed of the test piston as the fluid moves is used to determine and calculate the particulate count of contamination in the fluid. By monitoring the change in speed of the piston rod, the level of particulate matter is determined.

At the beginning of the stroke, the velocity of flow decreases only due to primary particles which are defined as particles larger than the size of the pores. Later, however, secondary particles are also caught by pores only partially blocked by primary particles. Secondary particles are defined as smaller particles that plug flow paths around larger primary particles. For a total blockage, tertiary size particles also play a role. Complete blockage of a screen, therefore, does not depend solely on particles larger than the pore openings, but on the total particle size distribution. From the progressive flow rate decay, an estimate of particles larger than certain sizes can be made depending on the known screen pore size.

Since blockage of a pore is normally not complete, fluid still flows through a pore partially blocked by a primary particle at the beginning of the flow. This is the secondary flow rate.

Each particle size distribution creates its own characteristic flow decay curve, which forms a fingerprint of the system by which it can be identified.

A back flush stroke is also included. A handle 52 extends from the device 50 and is connected to the test piston rod. The handle 52 is used to drive the test piston rod and test piston back into the initial position to begin another cycle and begin another test. The back flush stroke forces all of the fluid back in the reverse direction through the screen and back into the in-let line 40.

A reading is thereby achieved of all the solid particulate matter in the fluid.

Turning to FIG. 6, a second solid contamination level is determined. The device 10 of the present invention is inserted between the contamination measurement apparatus 50 and the fluid system. The sampling probe 11 is threadably connected to the inlet port 42 and the test port 13 is connected to measurement apparatus 50.

As fluid passes through the separator chamber 14 of the ferrous particle contamination apparatus 10, any ferrous particles will be drawn to and captured by the wire mesh media 15 which has been induced with a magnetic field.

The fluid thereafter passes into the contamination measurement apparatus 50. Accordingly, only non-ferrous particles will pass into the contamination measurement apparatus 50. The same procedure as previously described will be performed again in order to determine the non-ferrous contaminants in the fluid.

Thereafter, the total solid contamination is compared to or measured against the non-ferrous solid contamination. The difference between the two is the ferrous contamination level in the fluid.

The present invention also determines particle size distribution within the machine fluid system caused by wear.

The present invention calculates both particle count and particle size distribution using primary, secondary and tertiary blocking behavior of a particle-size distribution exposed to a calibrated single or mono size screen or micro-sieve. The sieve size (for instance, 5, 10 or 15 micron) is selected depending on the fluid and viscosity. From this data, an ISO cleanliness code is determined from a calibration formula. The invention is capable of providing an accurate count of particles at specific sizes with a single filter element. The invention determines the particle sizes and the particle size distribution. The particle size distribution is important in predicting and evaluating wear in a machine fluid system.

The two readings may be delivered to a central processing unit so that the difference is calculated and displayed on a monitor.

It will be appreciated that the process may also be performed in the reverse order. That is, the non-ferrous solid contamination level may be measured first. Thereafter, the total solid contamination level may be measured. Finally, the difference between the two is the level of ferrous contamination in the fluid.

As an alternate process, the ferrous particle counter 10 of the present invention may be left in place juxtaposed between the fluid system and the contamination measurement apparatus 50. In order to take the reading of total solid particulate matter, the knob 23 is rotated so that the magnet field is moved away from the separator chamber.

Figure 7:
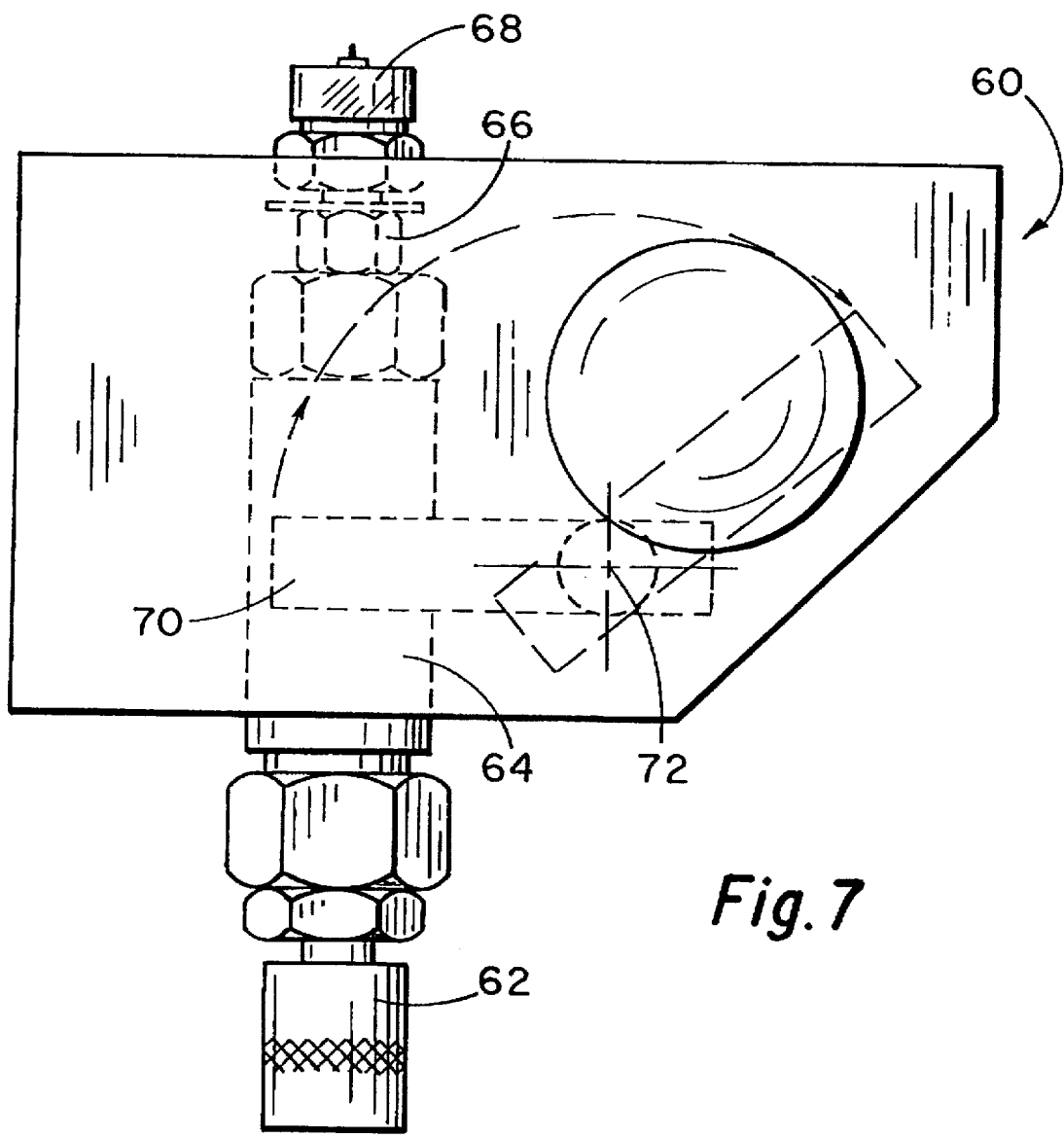
FIG. 7 is a perspective view of an alternate embodiment of the present invention.

It will also be appreciated that the ferrous particle counter 10 may be permanently secured to the measurement apparatus 50. FIG. 7 is an alternate embodiment 60 of the device to measure ferrous particle contamination in the fluid.

A sampling probe 62 is in fluid communication with a separator chamber 64 containing a wire mesh media or other ferrous media that may be magnetized. The apparatus 62 extends to an adapter 66 and terminates in a test port 68.

A magnet item 70 (shown by dashed lines) is used to induce a magnetic field. The magnet is attached to a rotor which pivots about a shaft 72 which provides an axis for rotation. In the first position, the magnet induces a magnetic field in the wire mesh media, thereby providing a magnetic force which attracts ferrous particles as previously described. In the opposed position, the magnetic field of the magnet does not pass into or through the separator chamber. It has been found that rotating the magnet rotor at least 180° about the axis removes the magnetic field from the wire mesh media.

Whereas, the present invention has been described in relation to the drawings attached hereto, it should be understood that other and further modifications, apart from those shown or suggested herein, may be made within the spirit and scope of this invention.

What is claimed is:

1. A method of determining ferrous particle contamination in a fluid within a machine fluid system caused by wear, which method comprises:

a. determining particle size distribution by counting solid particle contamination in a portion of said fluid to determine a solid contamination particle count above at least one given particle size;

b. separating ferrous particles from a portion of said fluid by passing through a ferrous mesh media magnetized by a magnetic field;

c. determining particle size distribution by counting solid particle contamination in said portion of fluid after separating said ferrous particles to determine a non-ferrous solid contamination particle count above at least one given particle size; and d. determining particle size distribution by comparing said solid contamination distribution with said non-ferrous solid contamination distribution to determine a ferrous particle distribution above at least one given particle size in said machine fluid system caused by wear.

2. A method of determining ferrous particle contamination as set forth in claim 1 wherein a portion of fluid from said fluid system is allowed to pass through a separator chamber containing a ferrous mesh media which is magnetized by said magnetic field.

3. A method of determining ferrous particle contamination as set forth in claim 2 wherein said separator chamber is connected by a sampling probe to said fluid system so that fluid from said system will pass through said probe and through said chamber.

4. A method of determining ferrous particle contamination as set forth in claim 1 wherein said magnetic field is induced by a permanent magnet outside of said separator chamber.

5. A method of determining ferrous particle contamination as set forth in claim 1 wherein said magnetic field is induced by an electromagnet outside of said separator chamber.

6. A method of determining ferrous particle contamination as set forth in claim 1 wherein said solid particle and said non-ferrous solid contamination levels are measured by flow decay rates of said fluid.

7. A method of determining ferrous particle count as set forth in claim 1 wherein said first and said second solid contamination levels are compared through a central processing unit.

8. A method of determining ferrous particle contamination in a fluid within a machine fluid system caused by wear, which method comprises:
   a. separating ferrous particles from a first portion of said fluid by passing through a ferrous mesh media magnetized by a magnetic field;
   b. determining particle size distribution by counting solid particle contamination in said first portion of fluid after removing said ferrous particles to determine a first solid contamination particle count above at least one given particle size;
   c. determining particle size distribution by counting solid particle contamination in a second portion of said fluid to determine a second solid contamination particle count above at least one given particle size; and
   d. determining particle size distribution by comparing said first solid contamination distribution with said second contamination distribution to determine a ferrous particle distribution above at least one given particle size in said machine fluid system caused by wear.

9. An apparatus to determine ferrous particle contamination in a fluid within a machine fluid system caused by wear, which apparatus comprises:
   a. means to determine particle size distribution by measuring solid particle contamination in said fluid to determine a first solid contamination particle count above at least one given particle size;
   b. means to separate ferrous particles from said fluid by passing through a ferrous mesh media magnetized by a magnetic field;
   c. means to determine particle size distribution by measuring solid particle contamination in said fluid after separating said ferrous particles to determine a second solid contamination count above at least one given particle size;
   d. means to compare said first solid contamination count with said second contamination count to determine a ferrous particle count above said at least one given particle size; and
   e. means to determine a particle size distribution from said ferrous particle count in (d) above at least one given particle size.

10. An apparatus to determine ferrous particle count in a fluid as set forth in claim 9 wherein said means to separate ferrous particles includes a separator chamber having ferrous mesh media therein and wherein said magnetic field is induced by a magnet outside said separator chamber.

11. A apparatus to determine ferrous particle count in a fluid as set forth in claim 10 wherein said magnet may be moved in a radial arc to move the magnetic field into or out of the separator chamber.

12. An apparatus to determine ferrous particle count in a fluid as set forth in claim 10 wherein said separator chamber is formed from a non-ferrous material.

13. An apparatus to determine ferrous particle count in a fluid as set forth in claim 9 wherein said means to measure solid particle contamination to determine said first and second particle counts includes a filter for passing said fluid there through and a means to determine flow degradation of said fluid.

* * * * *